United States Patent [19]

Sawatari et al.

[11] Patent Number: 4,677,847
[45] Date of Patent: Jul. 7, 1987

[54] AUTOMOTIVE ENGINE OIL MONITORING SYSTEM

[75] Inventors: Takeo Sawatari, Birmingham; Mitsutaka Nakamura, Farmington Hills; Toshihiro Sugiura, Birmingham, all of Mich.

[73] Assignee: Aisin Seiki Kabushiki Kaisha, Asahi, Japan

[21] Appl. No.: 781,501

[22] Filed: Sep. 30, 1985

[51] Int. Cl.⁴ .......................................... G01N 33/28
[52] U.S. Cl. ........................................ 73/64; 73/117.3
[58] Field of Search ................. 73/118, 53, 64, 117.3; 340/59

[56] References Cited

U.S. PATENT DOCUMENTS

| | | |
|---|---|---|
| 2,841,201 | 12/1957 | Cotton . |
| 3,049,964 | 8/1962 | Miller et al. .............................. 73/64 |
| 3,275,808 | 9/1966 | Knudsen . |
| 4,007,629 | 2/1977 | Hochstein ................................ 73/64 |
| 4,082,511 | 4/1978 | Bedford .................................. 73/64 |
| 4,311,041 | 1/1982 | Reid et al. ........................... 73/117.3 |
| 4,497,200 | 2/1985 | Tournier ................................. 73/64 |

FOREIGN PATENT DOCUMENTS 0072859  1/1980  Japan ........................................ 73/64

Primary Examiner—Michael J. Tokar
Assistant Examiner—Robert R. Raevis
Attorney, Agent, or Firm—Banner, Birch, McKie & Beckett

[57] ABSTRACT

The present invention describes a method and apparatus for monitoring and indicating engine oil deterioration during the period of the oil's useful life in an internal combustion engine. The system and method permits a determination of the rate of deterioration of the engine oil as a function of oil temperature or RPM of the engine and provides a continous output signal representing the remaining useful life of the oil which is provided to the driver when desired. The present invention therefore, estimates the time when the oil will reach an undesirable deterioration level during the course of operation of the engine rather than indicating, as many prior art systems, only when the oil reaches an undesirable level requiring an oil change.

8 Claims, 8 Drawing Figures

FIG. 8A
(CONTINUED FROM FIG. 8)
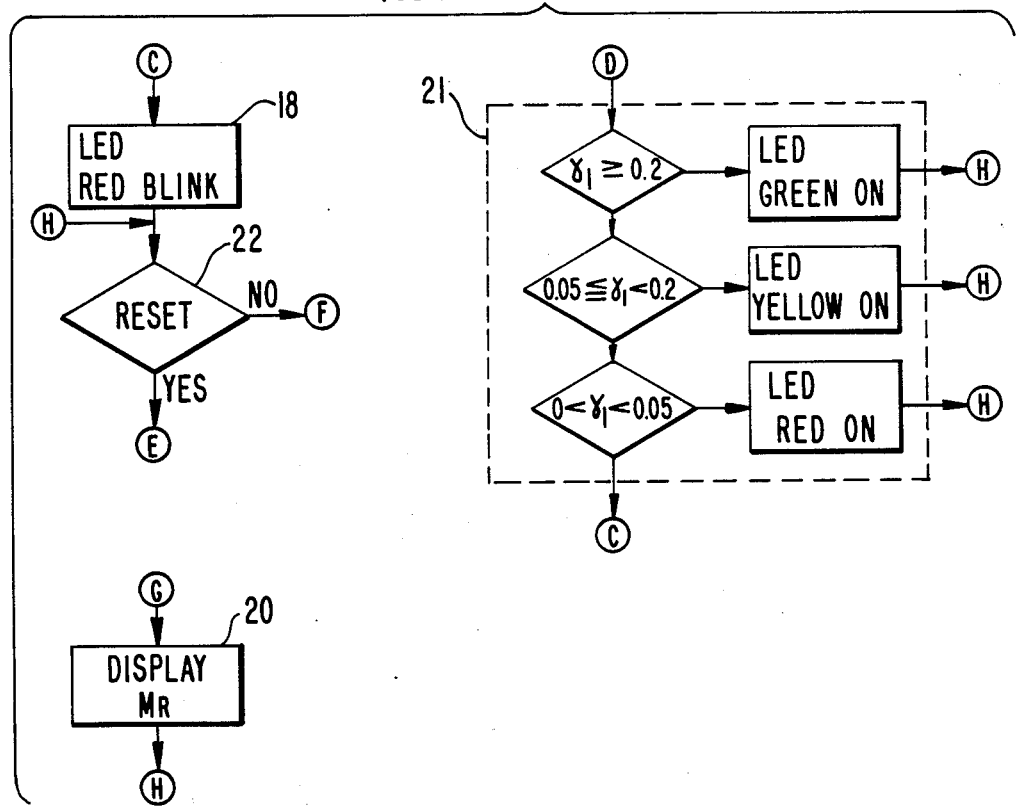

AUTOMOTIVE ENGINE OIL MONITORING SYSTEM

BACKGROUND OF THE INVENTION

The present invention relates to an automative engine oil deterioration monitoring system and more particularly provides an automative system to monitor engine oil which is capable of predicting the time, in the future, when the engine oil should be changed.

Hochstein U.S. Pat. No. 4,007,629 discloses a method and apparatus for monitoring oil degradation. The system incorporates an intricate mechanical structure which is subject to mechanical failure. However, according to this patent an alarm signal is provided only when the oil has already deteriorated to an undesirable level. It is more desirable for a driver to know in advance when he should change the engine oil by continuously monitoring the change in oil deterioration and determining the remaining useful life of the oil.

Unlike the above patented system, the present invention does not measure the oil deterioration directly but provides a system to continuously estimate the change in oil deterioration based on the oil temperature history or engine RPM history. The present invention, therefore, estimates the remaining time or mileage before the oil will reach an undesirable deterioration level.

There are various causes of oil deterioration. It has been discovered in accordance with the present invention, however, that engine oil temperature, engine running time and the time elapsed from the previous oil change are important parameters to estimate the degree of deterioration with respect to the following major causes of oil deterioration. First, oxidation of engine oil is one of the major causes of oil deterioration and the degree of oxidation is a function of temperature and time. If the temperature is high, the oxidation progresses faster and if the reaction time at a certain temperature is longer, more oxidation occurs. Second, oil molecules are broken by mechanical action, such as friction, between a piston and a cylinder. These molecular breaks produce sludge and decrease lubricity. This mechanical damage occurs more readily when the viscosity of the oil is low due to low temperature. This cause is also a function of temperature and time. A further cause of oil deterioration is the production of cinders of gasoline combustion. The production of cinders per unit of gasoline combustion contaminates oil; the amount of cinder per unit of gasoline combustion depends on engine conditions. Due to the recent advances in electronic fuel injection systems which reduce incomplete combustion and minimize cinder production, it is appropriate to consider that the amount of cinder production is simply proportional to the amount of total gasoline combustion. This total gasoline combustion is monitored by the RPM of the engine, oil temperature, and the engine running time. Monitored RPM can be converted as explained hereinafter.

Oil deterioration rate is also changed by driving conditions. For example, if an automobile is idling for a long period of time, driving faster than normal speed, or towing a heavy load, oil will deteriorate faster. These driving conditions are reflected in oil temperature. Monitoring oil temperature provides a reasonable basis for estimating oil deterioration due to such causes.

Besides the above mentioned causes, other factors can effect the rate of oil deterioration, such as air pollution and differences among oils and engines. The effect of these remaining factors, however, are not significant and have a secondary effect as compared with the previously mentioned major causes.

Consequently, engine oil temperature (or engine RPM), engine running time and elapsed time provide reasonable basis for estimating the degree of oil deterioration.

SUMMARY OF THE INVENTION

The present invention provides a system which continuously monitors engine running time or elapsed time and oil temperature or engine RPM to provide an indication of the extent of oil deterioration before the oil reaches a deterioration level requiring an oil change. An indication is provided, when desired by the driver, to show the remaining useful life of the oil which can be expressed in terms of remaining mileage, time or level of deterioration. The present invention provides a warning to a driver before the oil reads an undesirable deterioration level. The indication provided enables the driver to change the oil well in advance of the oil deterioration reading an undesirable level.

An object of the present invention is to provide an oil monitoring system which continuously provides an output signal representing the remaining useful life of oil.

An object of the present invention is to provide a simple monitoring system without utilizing complex mechanical structure to continuously monitor oil deterioration by measuring only RPM or oil temperature.

An object of the present invention is to estimate oil deterioration in a simple manner from oil temperature history or engine RPM history.

DESCRIPTION OF PREFERRED EMBODIMENTS

Figure 1:
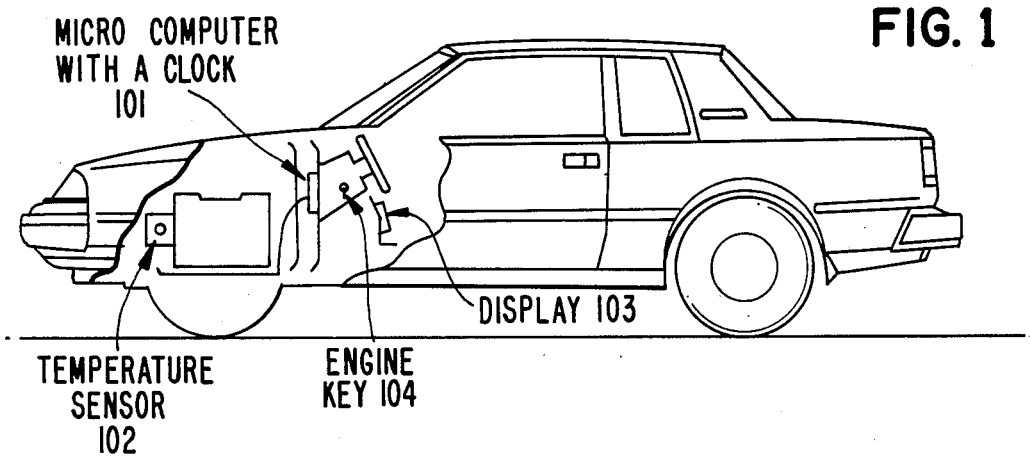
FIG. 1 is a diagram illustrating the subject invention installed in an automobile.

As seen in FIG. 1, an internal combustion engine oil monitoring system of the present invention is installed in an automobile. The system comprises a microcomputer 101 with a clock. Microcomputer 101 is installed adjacent the front panel of the dashboard where temperature conditions are suitable for the computer. The system also includes a temperature sensor 102 and display 103. Temperature sensor 102 is located in contact with the engine oil; temperature data read by microcomputer 101 via lead wires from temperature sensor 102. Display 103 is installed in the dashboard and connected to the output of microcomputer 101. Microcomputer 101 is also connected to the ignition key switch 104 to detect whether the engine is running.

Figure 2:
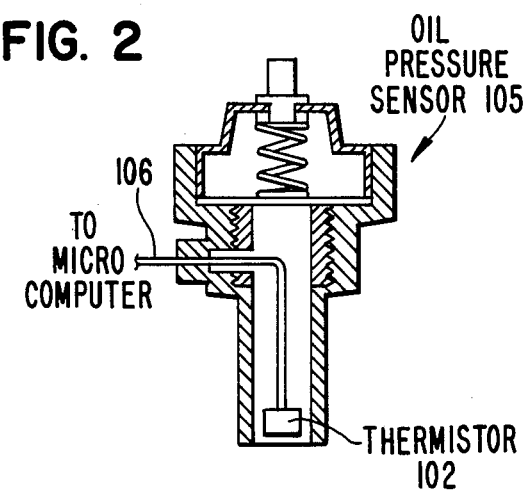
FIG. 2 is a diagram illustrating the location of a temperature sensor used in the subject invention.

FIG. 2 shows the structure of temperature sensor 102. In the preferred embodiment, a thermistor is used as part of temperature sensor 102 for sensing the temperature of the oil in accordance with the invention. It is positioned opposite the oil pressure sensor 105 within the temperature sensor housing; both the thermistor and sensor 105 are positioned to contact the engine oil. Temperature Sensor 102 has lead wires 106 for connection to microcomputer 101.

Figure 3:
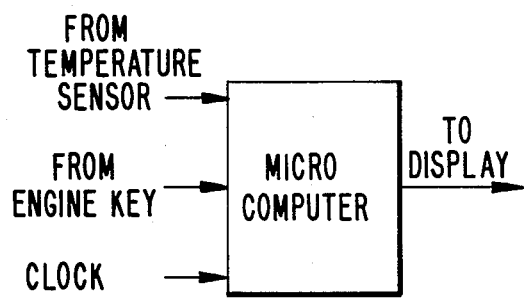
FIG. 3 is a diagram illustrating the inputs and output of a microcomputer used in the subject invention.

FIG. 3 illustrates inputs and output to and from microcomputer 101. Microcomputer 101 processes data received from temperature sensor 102, ignition key switch and an internal clock; the processed data is transmitted to display 103.

Figure 4:
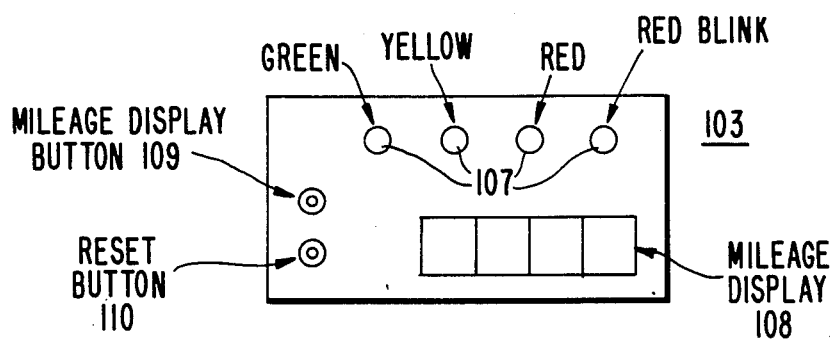
FIG. 4 is a diagram illustrating a display used in the subject invention.

FIG. 4 illustrates display 103. Display 103 has four LED lamps 107, comprising green, yellow, red and a blinking red display; each indicates the current status of engine oil deterioration. When an operator pushes mileage display button 109, mileage display 108 indicates the number of remaining miles that the car can travel before an oil change is required. The mileage display corresponds to the remaining useful life of the oil. Reset button 110 is pressed by an operator at the time the oil is changed so that microcomputer 101 initializes the data for the new oil.

The system uses two different kinds of parameters each of which indicates the degree of oil deterioration: an oil deterioration level A and the other is the oil's useful life B. Oil deterioration level A is the level of oil deterioration based on the record of oil temperature and the engine running time for that oil. When level A exceeds an undesirable level, occuring approximately at the end of the oil's useful life, an oil change is needed. A is derived from oil deterioration rate $\alpha$. $\alpha$ is a temperature-parameter and indicates the degree of oil deterioration when the engine is operated at a certain oil temperature for a unit time.

Figure 5:
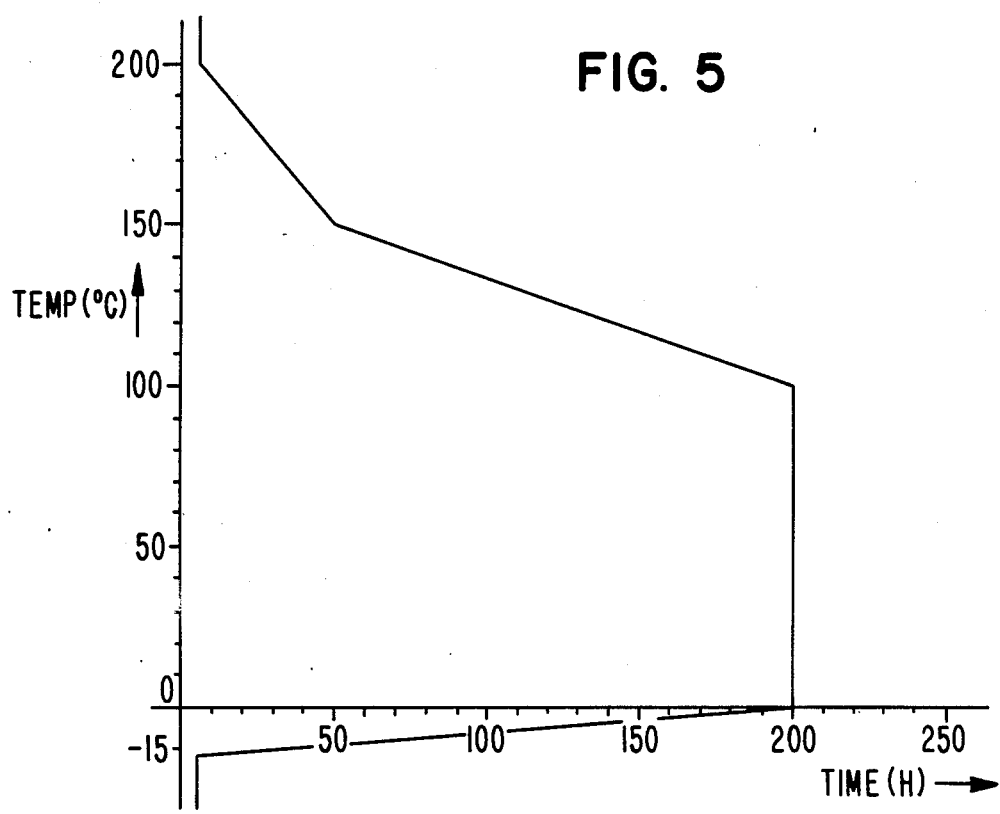
FIG. 5 is a graph illustrating the characteristics of oil temperature vs. time.

$\alpha$ is derived in the following manner. FIG. 5 is a graph which was obtained, in accordance with the invention, from experimental results analyzing oil longevity, while operated at certain temperatures. The graph was extrapolated and estimated from experimental test results on gasoline engines considering various types of oils, engine loads, engine size, oil temperature, and RPM history. For example, as shown in the graph, if oil temperature is maintained about 80° C., the oil will last approximately 200 hours of engine running time before it deteriorates to an undesirable level. If the engine is operated at an oil temperature of 150° C., the oil will last only 50 hours. However, in the high temperature region over 200° C., which is near the ignition point of oil, or in the low temperature region of below −15° C., where the viscosity of oil drastically reduces because of changes in molecular structure, the oil will last approximately 5 hours.

$\alpha$ is an inverse number of time represented by the graph in FIG. 5 for a certain temperature range; it represents the rate of oil deterioration of unit time for a corresponding temperature. Thus, based on FIG. 5, the following formulae of $\alpha$ in terms of temperature (T) are obtained:

$$\alpha \begin{cases} = \dfrac{1}{5} & T > 200, \\ = \dfrac{10}{1850 - 9T} & 200 \geq T > 150 \\ = \dfrac{1}{500 - 3T} & 150 \geq T > 100 \\ = \dfrac{1}{200} & 100 \geq T > 0 \\ = \dfrac{1}{200 + 13T} & 0 \geq T > -15 \\ = \dfrac{1}{5} & -15 \geq T \end{cases} \quad \text{Eq.-1}$$

wherein T: Engine oil temperature (°C.).

Oil deterioration level A is determined by the following equation:

$$A = \int_o^t \alpha(T)\, dt, \quad \text{Eq.-2}$$

wherein t: elapsed engine running time (hr).

A is determined from the data as to how long and under what oil temperature the engine has been operated. Thus, A represents a level of oil deterioration. When A reaches a predetermined threshold (e.g., A=1), it is established that the oil has deteriorated to an undesirable level. On the other hand, useful life B is a concept representing a shortened durable time of the engine oil. If the engine is operated only under normal conditions, the useful life of the oil is 12 months. However, if the engine is operated under severe conditions, that shortens the useful life. B is derived by the following equations:

$$\beta = 12 \left( \alpha - \dfrac{1}{200} \right) \quad \text{Eq.-3}$$

$$B = 12 - \int_o^t \beta\, dt \quad \text{Eq.-4}$$

In the above equations, $\alpha$ is defined by Eq.-1 and $\beta$ represents the reduction rate of the useful life of oil. If an engine is operated under normal contition, oil has a useful life of twelve (12) months. However, as the engine is operated under severe conditions than normal, it shortens the useful life of the oil.

In introducing Eq.-3, it is assumed that $\beta$ and $\alpha$ are linearly related, ($\beta = C_1 \alpha + C_2$). When the engine is operating under normal conditions, i.e., $\alpha = 1/200$ (from Eq.-1), $\beta$ must be zero; when the engine is operating at an oil temperature of 150° C., $\alpha = 1/50$ (from Eq.-1) and $\beta$ is 9/50. The reason why $\beta$ has been estimated as 9/50 is that oil deteriorates in only 3 months if the engine is operated under such conditions. That means reduction of the useful life by nine months. Further, because this reduction takes place in 50 hours of engine operation, the reduction rate for an hour of engine operation (i.e., $\beta$), is expressed as 9/50. By solving the linear equation using these boundary conditions, $C_1$ and $C_2$ are respectively obtained as 12 and −12/200.

B represents the useful life of the oil. As shown in Eq.-4, it is calculated by reducing the effect of severe driving operation that the engine has experienced since its previous oil change from the oil's normal useful life (i.e., twelve months). Accordingly, the time remaining for an oil change is given by $B-\tau$, wherein $\tau$ is the actual elapsed time measured from the time of oil change to the present whether or not the engine is operating. In other words, $B-\tau$ corresponds to the remaining useful life of the oil. When $B-\tau$ is equal to zero, the oil should be changed.

The reason why the calculation of B is required is that the engine oil has to be changed after a certain period of time even if the car has not been used. Just like the automobile instruction manual suggests to change oil, for example, every 12 months as well as every 8,000 miles, the system uses both parameters A and B. A relates to engine running time and mileage, while B relates to actual elapsed time; however, each is refined by temperature history data of the oil as explained above. The output indicator of display 103 is activated by the data based on A or B, whichever provides a higher deterioration level.

For a vehicle undergoing use during a time period, the longevity or useful life (B) of the oil can be expressed in terms of actual elapsed time, amount of oil deterioration, engine running time, or vehicle mileage. The remaining useful life is the time, mileage or level of deterioration remaining during the period of useful life, after a certain elapsed time or mileage, before an oil change is needed. For example, the useful life of oil is considered to be 12 months under ideal conditions $(100 \geq T > 0)$.

In order to implement the present invention, it is more practical if the time remaining for oil change (i.e., remaining useful life) is displayed in terms of the "remaining mileage" based on the values A and B of Eq.-2 and -4. Conversions in terms of mileage from A and B have been estimated by the following equations, assuming that an average car travels 8,000 miles in either 200 hours or 12 months:

(1) Estimated remaining mileage from A $$M_R = \frac{(1-A)}{A} \times t \times \frac{8000 \text{ (miles)}}{200 \text{ (hours)}} \qquad \text{Eq. 5}$$

(2) Estimated remaining mileage from B $$M_r = (B-\tau) \times \frac{8000 \text{ (miles)}}{12 \text{ (months)}}, \qquad \text{Eq. 6}$$

wherein
t: total engine running time (hour)
$\tau$: actual elapsed time (month).

Figure 6:
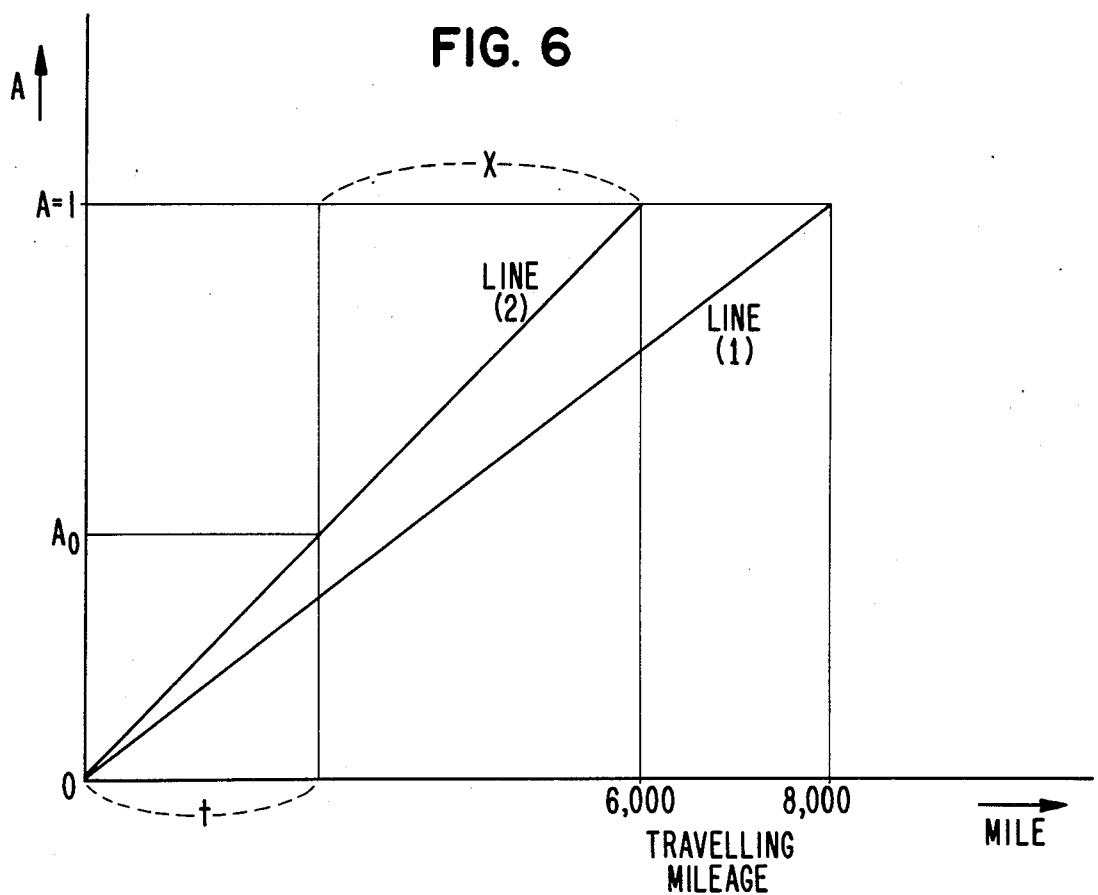
FIG. 6 is a graph illustrating the relationship between oil deterioration level A and traveling mileage.

$M_R$ is derived on the total engine running time (t); it corresponds to the remaining useful life of the oil. As shown in the graph of FIG. 6, which indicates relationship between the oil deterioration level A and traveling mileage, oil deterioration level A is proportional to traveling mileage assuming that the driving conditions (e.g., average speed, loading, etc.) are constant. Line (1) in FIG. 6 indicates an example if the driving conditions are normal; the traveled distance would be 8000 miles by the time the oil deterioration level A equals 1. Line (2) in FIG. 6 indicates a case where the driving conditions are more severe; the traveled distance is 6000 miles before the oil deteriorates to an undesirable level. Using the linear relation shown in FIG. 6, the remaining engine running time for oil change X at the moment $A = A_o$ is expressed in terms of total engine running time t:

$$X/(1-A_o) = t/A_o$$

This assumes, of course, that the vehicle will continue to travel under the same conditions as before. $M_R$ in Eq.-5 is obtained by multiplying the average speed of 40 miles/hour, or 8000 miles/200 hours which represents the standard mileage/standard total enging running time for a vehicle by the remaining runnning time for the oil to read the level of deterioration requiring an oil change.

$M_r$ on the other hand, is derived based on actual elapsed time $\tau$. $B-\tau$ is the time remaining for an oil change as explained above. $M_r$ in Eq.-6 is obtained by multiplying average mileage per month, or 8,000 miles/12 months which represents standard mileage/standard elapsed time for a vehicle by the remaining elapsed time before an oil change is needed.

Display 103 shown in FIG. 4 has four LED lamps consisting of green, yellow, red and blinking red. Each LED lamp may be used to indicate the following information:

(a) Green: Remaining mileage is more than 20% of the total mileage;
(b) Yellow: Remaining mileage is between 20% and 5% of the total mileage;
(c) Red: Remaining mileage is between 5% and 0% of the total mileage; and
(d) Blinking Red: No remaining mileage—an oil change is needed.

The above percentages can be determined from the following ratios:

$$\gamma_1 = M_R/M_{tR};$$

or $$\gamma_2 = M_r/M_{\tau r} \qquad \text{Eq.-7}$$

$M_{tR}$ and $M_{\tau r}$ in the above equations are defined as follows;

$$M_{tR} = t/A \times 8,000 \text{ (miles)}/200 \text{ (hours)};$$

and $$M_{\tau r} = B \times 8,000 \text{ (miles)}/12 \text{ (months)}. \qquad \text{Eq.-8}$$

These values represent the total mileage after an oil change that one can drive without being required to again change the oil. $M_{tR}$ is the total mileage determined from the total engine running time (t) and the oil determination level (A) of Eq.-2 assuming the average speed of a standard car is explained with regard to Eq.-5. $M_{\tau r}$ is the total mileage determined from the effective durable time B of Eq.-4, assuming the average mileage per month of a standard car as explained regarding Eq.-6.

As seen from Eq.-5, 6, 7 and 8, $\gamma_1$, and $\gamma_2$ are also described as:

$$\gamma_1 = 1 - A;$$

and $$\gamma_2 = (B-\tau)/B \qquad \text{Eq.-9}$$

Consequently, $\gamma_1$ and $\gamma_2$ are independent of the assumed average speed of vehicle.

It is desirable to calculate both $\gamma_1$ and $\gamma_2$ since an engine can sit idle for a long time. An oil change would be needed if the actual elapsed time is sufficiently large and, therefore, $M_r$ is necessary to indicate this condition.

Display 103 displays the remaining mileage on mileage display 108 (FIG. 4). The system of the present invention selects the smaller of the two ratios, as discussed below. Thus, either $M_R$ or $M_r$ is displayed corresponding to the smaller of $\gamma_1$ or $\gamma_2$.

Figure 8:
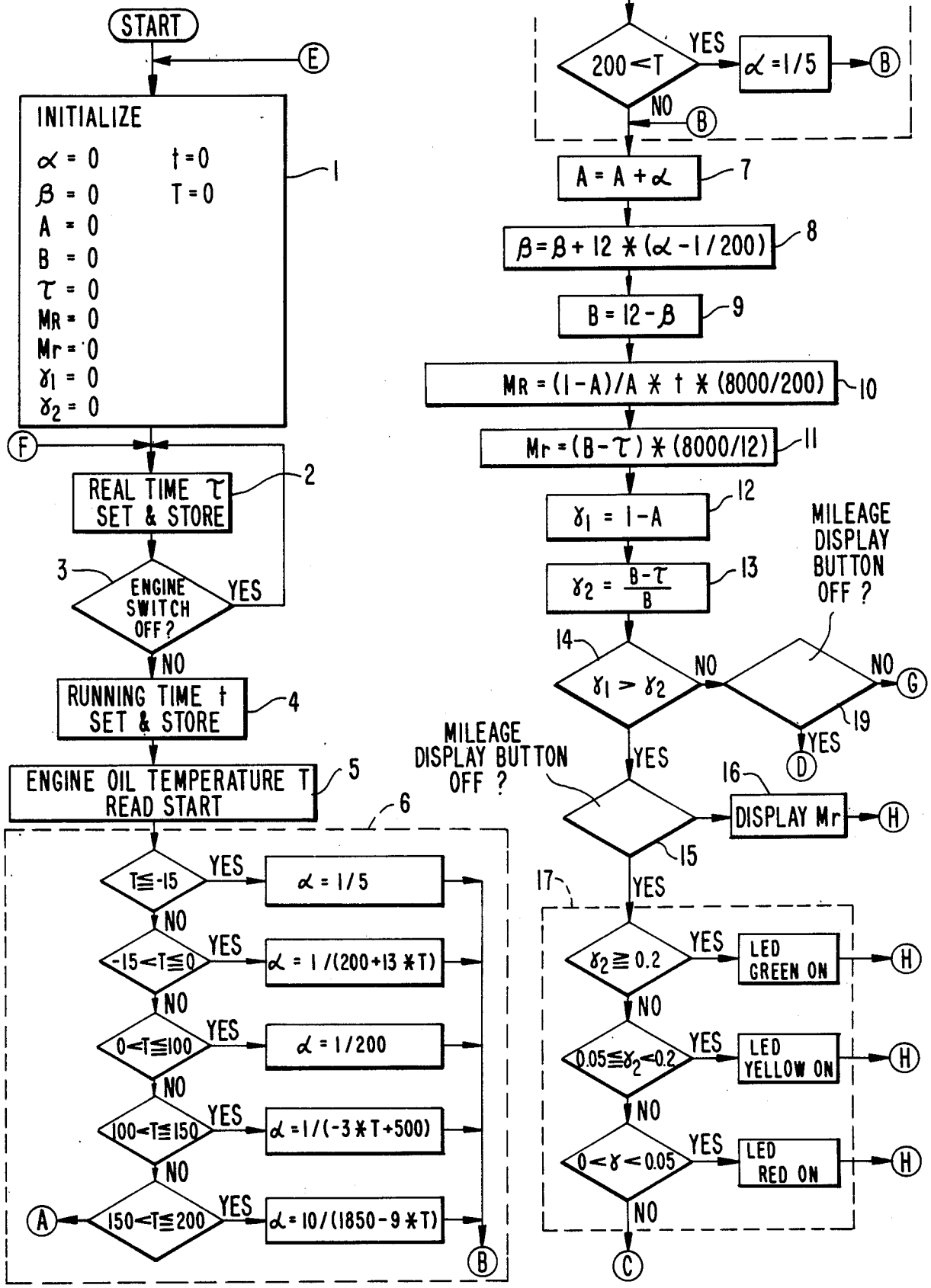
FIG. 8 is a flowchart used in the subject invention.

FIG. 8 is a flowchart of the program which process the preferred embodiment of the present invention. At step 1, the microcomputer initializes to zero the following variables: $\gamma$, $\beta$, A, B, $\tau$, $M_r$, $M_R$, $\gamma_1$, $\gamma_2$, t and T. At step 2, real time $\tau$ is set and stored so that $\tau$ has a data representing actual elapsing time from the initialization. The computer includes a clock for measuring the actual elapsed time. At step 3, microcomputer reads the state of the engine key switch; if it is off, the system returns to step 2 and the loop of steps 2 and 3 are repeated until the engine key switch is turned on. At step 4, time is set and stored in t so that it contains data representing the total engine running time from initialization. Therefore, the computer includes a further clock for measuring and storing the actual engine running time.

At step 5, microcomputer reads the engine oil temperature T signal generated by temperature sensor 102. At step 6, depending on the range of T, a certain value representing the rate of oil deterioration in accordance with Eq.-1 is stored in $\alpha$. The comparison and selection operation of step 6 determines the deterioration rate of the oil. At step 7, data $\alpha$ is accumulated in A each time this step is processed and A will have an integrated value of $\alpha$ as shown by Eq.-2. At step 8 data $\beta$ (Eq.-3) derived from $\alpha$ is accumulated in $\beta$ each time this step is processed and $\beta$ will have an integrated value of $12\times(\alpha-1/200)$. At step 9, the system determines the useful life of the oil; B has data representing useful life as shown by Eq.-4. At steps 10 and 11, a first remaining useful life ($M_r$) and a second remaining useful life ($M_R$) are determined by the system; $M_R$ and $M_r$ are calculated based on data A, B, t and $\tau$ from equations Eq.-5 and 6. At steps 12 and 13; a first ratio is determined based upon actual elapsed time and a second ratio is determined based upon engine running time; $\gamma_1$ and $\gamma_2$ are calculated by using Eq.-9. At step 14 $\gamma_1$ and $\gamma_2$ are compared and if $\gamma_1$ is greater than $\gamma_2$ the microcomputer determines if the mileage display is pushed. If pushed, the data in $M_r$ is displayed (step 16). If not pushed, at steps 17 and 18, depending on the range of $\gamma_2$ one of four LED lamp is turned on. If (at step 14) $\gamma_1$ is not greater than $\gamma_2$, than (at step 19) the microcomputer determines if the mileage display button is pushed. The system at step 14 provides an operation for selecting the smaller of $\gamma_1$ or $\gamma_2$. If pushed, (at step 20) the data in $M_R$ is displayed. If not pushed, (at steps 21 and 18), depending the range of $\gamma_1$, one of four LED lamp is turned on. After either one of steps 16, 17, 18, 20 or 21, the microcomputer checks (at step 22) if the Reset button is pushed. If the reset button is not pushed, the microcomputer returns to step 2 and repeats the process again. However, if the reset button is pushed, the microprocessor returns to step 1 and, after initializing all the variables, repeats the process again.

Figure 7:
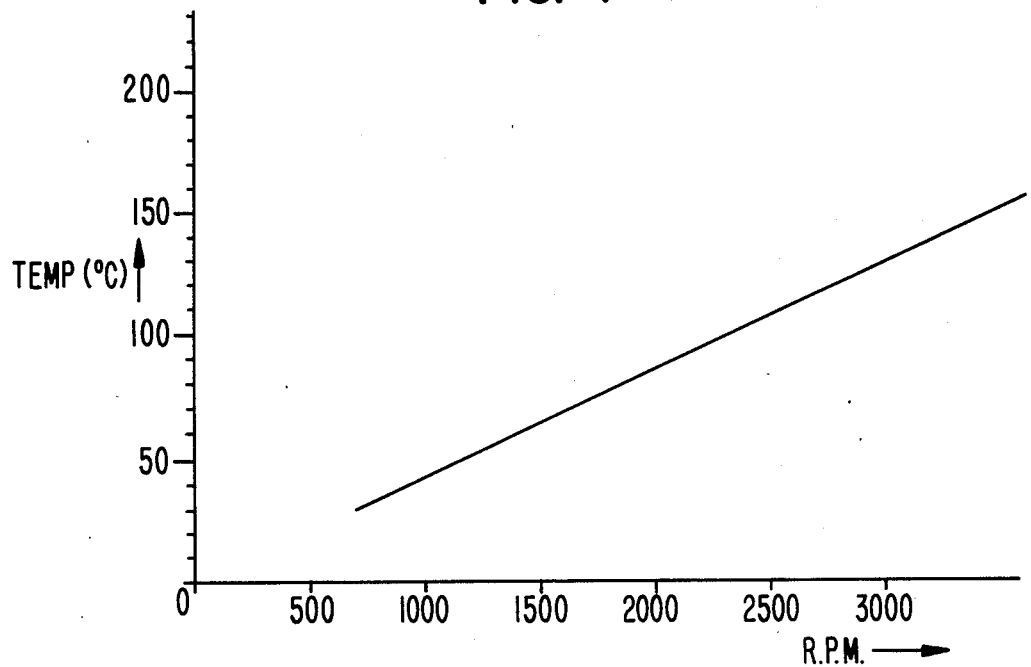
FIG. 7 is a graphic illustrating the relationship between engine oil temperature and engine RPM.

It should be noted that in the other preferred embodiment the input data of oil temperature may be replaced by a tachometer output since temperature and engine RPM are proportional, as shown in FIG. 7. Thus, the measured RPM can be converted to temperature and equations 1 through 9 can then be processed as previously described.

Further, variations and substitutions of equivalents may be made without departing in any way from the scope of the invention as defined in the appended claims.

We claim:

1. A method for continuously monitoring and indicating engine oil deterioration during the period of the oil's useful life in an internal combustion engine comprising the steps of:

generating a signal representative of engine oil temperature;

determining the rate of the deterioration of said oil as a function of oil temperature;

generating a signal representative of elapsed engine running time;

generating a signal representative of actual elapsed time since the oil was changed;

determining a first remaining useful life ($M_R$) of said oil as a function of said rate of deterioration and said elapsed engine running time from the expression:

$$M_R = \frac{1-A}{A} \times t \times \frac{8000 \text{ (miles)}}{200 \text{ (hours)}},$$

where $$A = \int_0^t \alpha(T)dt;$$

t = elapsed engine running time
T = oil temperature
$\alpha$ = oil deterioration rate and producing a continuous output signal representative of said first remaining useful life;

determining a second remaining useful life of said oil as a function of said rate of deterioration and said actual elapsed time and producing a continuous output signal representative of said second remaining useful life;

selecting either the continuous output signal from said elapsed engine running time and said rate of deterioration or the continuous output signal produced from said actual elapsed time and said rate of deterioration; and indicating the remaining useful life as a function of the selected output signal.

2. The method of claim 1 wherein the second remaining useful life ($M_r$) is determined from the expression:

$$M_R = (B - \tau) \times \frac{8000 \text{ (miles)}}{12 \text{ (months)}},$$

where:

$$B = 12 - \int_0^t [12(\alpha - 1/200)]dt,$$

where:

$\tau$ = actual elapsed time
$\alpha$ = oil deterioration rate.

3. A system for continuously monitoring and indicating engine oil deterioration during the period of the oil's useful life in an internal combustion engine comprising:

temperature signal generating means for generating a signal representative of engine oil temperature;

deterioration rate measuring means coupled to said temperature signal generating means for determining the rate of deterioration of said oil as a function of oil temperature;

engine running time measuring means for generating a signal representative of elapsed engine running time;

time measuring means for generating a signal representative of actual elapsed time since the oil was changed;

a first remaining useful life determining means coupled to said deterioration rate determining means and said engine running time measuring means for determining the first remaining useful life ($M_R$) in accordance with the following expression:

$$M_R = \frac{1-A}{A} \times t \times \frac{8000 \text{ (miles)}}{200 \text{ (hours)}},$$

where $$A = \int_0^t \alpha(T)dt;$$

t = elapsed engine running time
T = oil temperature
$\alpha$ = oil deterioration rate, and producing a continuous output signal representative of said first remaining useful life;

a second remaining useful life determining means coupled to said deterioration rate determining means and said time measuring means for determining the second remaining useful life of said oil as a function of said deterioration rate and said actual elapsed time and producing a continuous output signal representative of said second remaining useful life;

signal selecting means for selecting either the output signal from the first remaining useful life determining means or the output signal from the second remaining useful life determining means; and indicating means coupled to said remaining useful life determining means for indicating the remaining useful life as a function of the selected output signal.

4. The system of claim 3 wherein the second remaining useful life ($M_r$) is determined from the expression:

$$M_R = (B - \tau) \times \frac{8000 \text{ (miles)}}{12 \text{ (months)}},$$

where:

$$B = 12 - \int_0^t [12(\alpha - 1/200)]dt,$$

where:
$\tau$ = actual elapsed time
$\alpha$ = oil deterioration rate.

5. A method for continuously monitoring and indicating engine oil deterioration during the period of the oil's life in an internal combustion engine comprising the steps of:

generating a signal representative of engine oil temperature;

determining the rate of the deterioration of said oil as a function of oil temperature;

generating a signal representative of elapsed engine running time;

generating a signal representative of actual elapsed time since the oil was changed;

determining a first remaining useful life ($M_R$) of said oil as a function of said rate of deterioration and said elapsed engine running time from the expression:

$$M_R = \frac{1-A}{A} \times t \times M,$$

where $$A = \int_0^t \alpha(T)dt;$$

t = elapsed engine running time
T = oil temperature
$\alpha$ = oil deterioration rate
M = a constant representative of average mileage of an automobile in miles/hour and producing a continuous output signal representative of said first remaining useful life;

determining a second remaining useful life of said oil as a function of said rate of deterioration and said actual elapsed time and producing a continuous output signal representative of said second remaining useful life;

selecting either the continuous output signal from said elapsed engine running time and said rate of deterioration or the continuous output signal produced from said actual elapsed time and said rate of deterioration; and indicating the remaining useful life as a function of the selected output signal.

6. The method of claim 5 wherein the second remaining useful life ($M_r$) is determined from the expression:

$$M_R = (B - \tau) \times M',$$

where $$B = C - \int_0^t \beta dt$$

c = a constant representative of the oil's normal useful life
$\beta$ = reduction rate of the useful life of the oil derived from the oil deterioration rate
t = elapsed engine running time
$\tau$ = actual elapsed time
M' = a constant representative of average mileage of an automobile in miles/month.

7. A system for continuously monitoring and indicating engine oil deterioration during the period of the oil's useful life in an internal combustion engine comprising:

temperature signal generating means for generating a signal representative of engine oil temperature;

deterioration rate measuring means coupled to said temperature signal generating means for determining the rate of deterioration of said oil as a function of oil temperature;

engine running time measuring means for generating a signal representative of elapsed engine running time;

time measuring means for generating a signal representative of actual elapsed time since the oil was changed;

a first remaining useful life determining means coupled to said deterioration rate determining means and said engine running time measuring means for determining the first remaining useful life ($M_R$) in accordance with the following expression:

$$M_R = \frac{1-A}{A} \times t \times M,$$

where $$A = \int_0^t \alpha(T)dt;$$

t = elapsed engine running time
T = oil temperature
α = oil deterioration rate
M = a constant representative of average mileage of an automobile in miles/hour, and producing a continuous output signal representative of said first remaining useful life;

a second remaining useful life determining means coupled to said deterioration rate determining means and said time measuring means for determining the second remaining useful life of said oil as a function of said deterioration rate and said actual elapsed time and producing a continuous output signal representative of said second remaining useful life;

signal selecting means for selecting either the output signal from the first remaining useful life determining means or the output signal from the second remaining useful life detering means; and indicating means coupled to said remaining useful life determining means for indicating the remaining useful life as a function of the selected output signal.

8. The system of claim 7 wherein the second remaining useful life ($M_r$) is determined from the expression:

$$M_r = (B - \tau) \times M',$$

where $$B = C - \int_0^t \beta dt$$

C = a constant representative of the oil's normal useful life
β = reduction rate of the useful life of the oil derived from the oil deterioration rate
t = elapsed engine running time
τ = actual elapsed time
M' = a constant representative of average mileage of an automobile in miles/month.

* * * * *

UNITED STATES PATENT AND TRADEMARK OFFICE
CERTIFICATE OF CORRECTION

PATENT NO. : 4,677,847

DATED : July 7, 1987

INVENTOR(S) : Takeo Sawatari, Mitsutaka Nakamura and Toshihiro Sugiura

It is certified that error appears in the above-identified patent and that said Letters Patent is hereby corrected as shown below:

Title page:

Please correct the Assignee as follows:

-- Aisin Seiki Kabushiki Kaisha, Kariya City, Japan --

Signed and Sealed this

Twenty-third Day of February, 1988

Attest:

DONALD J. QUIGG

*Attesting Officer*  *Commissioner of Patents and Trademarks*